(12) United States Patent
Tanoue et al.

(10) Patent No.: US 8,426,461 B2
(45) Date of Patent: Apr. 23, 2013

(54) ORALLY DISPERSIBLE TABLET

(75) Inventors: Yutaka Tanoue, Zurich (CH); Tetsuya Matsuura, Osaka (JP); Yutaka Yamagata, Osaka (JP); Naoki Nagahara, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/491,887

(22) Filed: Jun. 8, 2012

(65) Prior Publication Data

US 2012/0244223 A1 Sep. 27, 2012

Related U.S. Application Data

(63) Continuation of application No. 13/261,266, filed as application No. PCT/JP2012/051279 on Jan. 16, 2012.

(30) Foreign Application Priority Data

Jan. 17, 2011 (JP) .................................. 2011-007371
Oct. 14, 2011 (JP) .................................. 2011-227333

(51) Int. Cl.
*A01N 43/08* (2006.01)
*A61K 31/34* (2006.01)
*C07D 307/92* (2006.01)

(52) U.S. Cl.
USPC .......................................... 514/468; 549/458

(58) Field of Classification Search ................ 514/468; 549/458
See application file for complete search history.

(56) References Cited

U.S. PATENT DOCUMENTS

| 6,034,239 A | 3/2000 | Ohkawa et al. |
| 2001/0014340 A1 | 8/2001 | Ohta et al. |
| 2005/0131071 A1 | 6/2005 | Wuthrich et al. |
| 2007/0134331 A1 | 6/2007 | Julien et al. |
| 2009/0042861 A1 | 2/2009 | Hirai et al. |
| 2010/0098756 A1 | 4/2010 | Matsuoka et al. |
| 2011/0130428 A1 | 6/2011 | Lindahl et al. |

FOREIGN PATENT DOCUMENTS

| EP | 1 153 616 A1 | 11/2001 |
| EP | 1 867 641 A1 | 12/2007 |
| JP | 2005-523253 A | 8/2005 |
| JP | 2007-182440 A | 7/2007 |
| WO | WO 97/47287 A1 | 12/1997 |
| WO | WO 99/59544 A2 | 11/1999 |
| WO | WO 00/47233 A1 | 8/2000 |
| WO | WO 01/76565 A1 | 10/2001 |
| WO | WO 2007/137227 A1 | 11/2007 |
| WO | WO 2008083204 A2 * | 7/2008 |
| WO | WO 2008/120548 A2 | 10/2008 |

OTHER PUBLICATIONS http://www.medterms.com/script/main/art.asp?articlekey=12063.*
http://www.webmd.com/bipolar-disorder/tc/bipolar-disorder-prevention.*
Hilty et. al., Psychiatry (Edgmont), 2006, PubMed, vol. 3, issue 9, pp. 43-55.*
ClinicalTrials.gov, NCT00552760, "Ramelteon for the Treatment of Insomnia and Mood Stability in Patients with Euthymic Bipolar Disorder (Ram-TIME)," First received Oct. 31, 2007, last updated Jun. 1, 2010, 14 pages.
Citrome, L., "Asenapine for schizophrenia and bipolar disorder: a review of the efficacy and safety profile for this newly approved sublingually absorbed second-generation antipsychotic," Int. J. Clin. Pract., Dec. 2009 [epub Oct. 14, 2009], 63(12):1762-1784.
Vogt et al., "Pharmacokinetics and haemodynamic effects of ISDN following different dosage forms and routes of administration," European Journal of Clinical Pharmacology, 1994, 46(4):319-324.
Mueller-Oerlinghausen et al., "Bipolar disorder," The Lancet, Jan. 19, 2002, 359:241-247.

* cited by examiner

*Primary Examiner* — Sreeni Padmanabhan
*Assistant Examiner* — Sarah Pihonak
(74) *Attorney, Agent, or Firm* — Foley & Lardner LLP

(57) ABSTRACT

The present invention provides a preparation with improved disintegration property, a preparation showing improved bioavailability of a medicament, production methods thereof and the like. A rapidly disintegrating preparation comprising granules comprising a medicament coated with a coating layer containing sugar or sugar alcohol; and a disintegrant. A production method of a rapidly disintegrating preparation including a step of producing granules comprising a medicament, a step of forming a coating layer containing sugar or sugar alcohol on the obtained granules and a step of mixing the coated granules with a disintegrant and molding the mixture.

10 Claims, No Drawings

ORALLY DISPERSIBLE TABLET

CROSS-REFERENCE TO RELATED APPLICATIONS

This application is a Continuation of U.S. application Ser. No. 13/261,266, which is the U.S. National Stage of PCT/JP2012/051279, filed Jan. 16, 2012, which claims priority to Japanese Patent Application Nos. 2011-007371, filed Jan. 17, 2011, and 2011-227333, filed Oct. 14, 2011, the contents of which are incorporated in full herein.

BACKGROUND OF THE INVENTION

1. Technical Field

The present invention relates to a preparation with improved disintegration property, a preparation with improved bioavailability of medicament, production methods thereof and the like.

2. Description of Related Art

Patent document 1 discloses a tablet containing sugar alcohol or saccharide having an average particle size of 30 μm or below, an active ingredient and a disintegrant, and a production method of a tablet comprising compression molding a mixture containing sugar alcohol or sugar having an average particle size of 30 μm or below, an active ingredient and a disintegrant.

Patent document 2 discloses an orally dispersible solid pharmaceutical composition of agomelatine, which contains agomelatine and granules of simultaneously-dried lactose and starch.

Patent document 3 discloses an orally dispersible, coated solid pharmaceutical composition of agomelatine, which contains a central core or a central layer comprising agomelatine and excipients allowing an orally dispersible formulation to be obtained, and an orally dispersible coating.

However, patent documents 1-3 do not disclose improvement of preparation characteristics such as disintegration property and the like by enclosing components such as masking agent, binder and the like that prevent disintegration in granules.

DOCUMENT LIST

Patent Documents patent document 1: WO1997/047287
patent document 2: JP-A-2005-523253
patent document 3: JP-A-2007-182440

SUMMARY OF THE INVENTION

Problems to be Solved by the Invention

An object of the present invention is to provide a novel formulation technique capable of improving disintegration property. In addition, another object of the present invention is to provide a preparation useful as an orally rapidly disintegrating preparation. Moreover, an object of the present invention is to provide a preparation capable of promoting medicament absorption from the oral mucosa by rapid disintegration after sublingual administration, and improving the medicament bioavailability.

Means of Solving the Problems

The present inventors have conducted intensive studies in an attempt to solve the aforementioned problems and found that the disintegration property of a medicament can be improved and the bioavailability thereof can also be improved by containing a component that prevents disintegration (masking agent, binder and the like) as a granulation component in granules, and formulating the preparation after coating a surface of the granule with sugar or sugar alcohol, which resulted in the completion of the present invention.

Accordingly, the present invention provides the following.

[1] A rapidly disintegrating preparation comprising granules comprising a medicament coated with a coating layer containing sugar or sugar alcohol; and a disintegrant (hereinafter sometimes to be abbreviated as preparation [1], the same for the following [2] to [18]).

[2] The rapidly disintegrating preparation of the above-mentioned [1], wherein the granules comprising a medicament further contains a binder.

[3] The rapidly disintegrating preparation of the above-mentioned [1], wherein the granules comprising a medicament further contains a masking agent.

[4] The rapidly disintegrating preparation of the above-mentioned [1], wherein the granules comprising a medicament further contains a solubilizer.

[4-1] The rapidly disintegrating preparation of any of the above-mentioned [1]-[4], wherein the disintegration time is not more than 30 sec.

[4-2] The rapidly disintegrating preparation of any of the above-mentioned [1]-[4], wherein the disintegration time is not more than 30 sec and the absolute hardness is not less than $1.0 \text{ N/mm}^2$.

The "rapidly disintegrating preparation" of the present invention is also superior as a preparation for allowing absorption of a medicament from the oral mucosa. Specifically, it is as described below.

[5] The preparation of any of the above-mentioned [1]-[4], which is for oral-mucosal absorption.

[6] The preparation of the above-mentioned [5], wherein the medicament is (S)—N-[2-(1,6,7,8-tetrahydro-2H-indeno[5,4-b]furan-8-yl)ethyl]propionamide (general name ramelteon; hereinafter sometimes to be abbreviated as compound A).

[7] The preparation of the above-mentioned [5] or [6], which is a tablet.

[8] A method of producing a rapidly disintegrating preparation, comprising a step of producing granules comprising a medicament, a step of forming a coating layer containing sugar or sugar alcohol on the obtained granules, and a step of mixing the coated granules with a disintegrant and molding the mixture.

In addition to the above-mentioned preparation [6], the present inventors have conducted intensive studies of a preparation superior in the absorption of compound A from the oral mucosa, and showing improved bioavailability thereof, and complete the following invention.

[9] A preparation for oral-mucosal absorption comprising (S)—N-[2-(1,6,7,8-tetrahydro-2H-indeno[5,4-b]furan-8-yl)ethyl]propionamide as a medicament; which shows a higher ratio of the medicament in an unchanged form and a metabolite of the medicament (i.e., medicament in unchanged form/metabolite of the medicament) after transfer into blood than that by oral administration.

[10] A preparation for oral-mucosal absorption comprising (S)—N-[2-(1,6,7,8-tetrahydro-2H-indeno[5,4-b]furan-8-yl)ethyl]propionamide as a medicament; which shows a higher ratio of the medicament in an unchanged form and a metabolite of the medicament after transfer into blood than that by oral administration, and a disintegration time of not more than 30 sec.

[11] A preparation for oral-mucosal absorption comprising (S)—N-[2-(1,6,7,8-tetrahydro-2H-indeno[5,4-b]furan-8-yl)ethyl]propionamide as a medicament; which shows a higher ratio of the medicament in an unchanged form and a metabolite of the medicament after transfer into blood than that by oral administration, a disintegration time of not more than 30 sec, and absolute hardness of not less than 1.0 N/mm$^2$.

[12] A preparation for oral-mucosal absorption comprising (S)—N-[2-(1,6,7,8-tetrahydro-2H-indeno[5,4-b]furan-8-yl)ethyl]propionamide and a masking agent; which shows not less than about 10-fold improved bioavailability of (S)—N-[2-(1,6,7,8-tetrahydro-2H-indeno[5,4-b]furan-8-yl)ethyl]propionamide, as compared to that by oral administration.

[13] A preparation for oral-mucosal absorption comprising (S)—N-[2-(1,6,7,8-tetrahydro-2H-indeno[5,4-b]furan-8-yl)ethyl]propionamide and a masking agent; which shows not less than about 10-fold improved bioavailability of (S)—N-[2-(1,6,7,8-tetrahydro-2H-indeno[5,4-b]furan-8-yl)ethyl]propionamide, as compared to that by oral administration, and a disintegration time of not more than 30 sec.

[14] A preparation for oral-mucosal absorption comprising (S)—N-[2-(1,6,7,8-tetrahydro-2H-indeno[5,4-b]furan-8-yl)ethyl]propionamide and a masking agent; which shows not less than about 10-fold improved bioavailability of (S)—N-[2-(1,6,7,8-tetrahydro-2H-indeno[5,4-b]furan-8-yl)ethyl]propionamide, as compared to that by oral administration, a disintegration time of not more than 30 sec, and absolute hardness of not less than 1.0 N/mm$^2$.

[15] A preparation for oral-mucosal absorption comprising (S)—N-[2-(1,6,7,8-tetrahydro-2H-indeno[5,4-b]furan-8-yl)ethyl]propionamide, sugar or sugar alcohol, and a disintegrant; which shows not less than about 10-fold improved bioavailability of (S)—N-[2-(1,6,7,8-tetrahydro-2H-indeno[5,4-b]furan-8-yl)ethyl]propionamide, as compared to that by oral administration, and a disintegration time of not more than 30 sec.

[16] A preparation for oral-mucosal absorption comprising (S)—N-[2-(1,6,7,8-tetrahydro-2H-indeno[5,4-b]furan-8-yl)ethyl]propionamide, sugar or sugar alcohol, and a disintegrant; which shows not less than about 10-fold improved bioavailability of (S)—N-[2-(1,6,7,8-tetrahydro-2H-indeno[5,4-b]furan-8-yl)ethyl]propionamide, as compared to that by oral administration, a disintegration time of not more than 30 sec, and absolute hardness of not less than 1.0 N/mm$^2$.

[17] The preparation of any of the above-mentioned [9]-[16], which is a tablet.

[18] The preparation of the above-mentioned [9] or [12], which is in the form of a film, troche, solution, suspension, freeze-dried preparation, chewing gum or spray.

[19] A method for the prophylaxis and/or treatment of a bipolar disorder comprising administering (S)—N-[2-(1,6,7,8-tetrahydro-2H-indeno [5,4-b]furan-8-yl)ethyl]propionamide oral-mucosally to a human.

[20] The method of the above-mentioned [19], wherein the oral-mucosal administration is sublingual administration or buccal administration (more preferably sublingual administration).

[21] The method of the above-mentioned [19], wherein (S)—N-[2-(1,6,7,8-tetrahydro-2H-indeno[5,4-b]furan-8-yl)ethyl]propionamide is administered in 0.05-1.0 mg per day.

[22] The method of the above-mentioned [19], wherein the bipolar disorder is bipolar disorder I.

[23] The method of the above-mentioned [19], wherein the prophylaxis and/or treatment of a bipolar disorder is a treatment of a depression symptom associated with the bipolar disorder or maintenance of a remission phase of the bipolar disorder.

[24] A drug for the prophylaxis and/or treatment of a bipolar disorder, which comprises, as an active ingredient, (S)—N-[2-(1,6,7,8-tetrahydro-2H-indeno[5,4-b]furan-8-yl)ethyl]propionamide to be oral-mucosally administered to a human.

[25] The drug of the above-mentioned [24], wherein the oral-mucosal administration is sublingual administration or buccal administration (more preferably sublingual administration).

[26] The drug of the above-mentioned [24], wherein (S)—N-[2-(1,6,7,8-tetrahydro-2H-indeno[5,4-b]furan-8-yl)ethyl]propionamide is administered in 0.05-1.0 mg per day.

[27] The drug of the above-mentioned [24], wherein the bipolar disorder is bipolar disorder I.

[28] The method of the above-mentioned [24], wherein the prophylaxis and/or treatment of a bipolar disorder is a treatment of a depression symptom associated with the bipolar disorder or maintenance of a remission phase of the bipolar disorder.

[29] (S)—N-[2-(1,6,7,8-tetrahydro-2H-indeno[5,4-b]furan-8-yl)ethyl]propionamide for the prophylaxis and/or treatment of a bipolar disorder by oral-mucosal administration to a human.

[30] The (S)—N-[2-(1,6,7,8-tetrahydro-2H-indeno [5,4-b]furan-8-yl)ethyl]propionamide of the above-mentioned [29], wherein the oral-mucosal administration is sublingual administration or buccal administration (more preferably sublingual administration).

[31] The (S)—N-[2-(1,6,7,8-tetrahydro-2H-indeno[5,4-b]furan-8-yl)ethyl]propionamide of the above-mentioned [29], which is administered in 0.05-1.0 mg per day.

[32] The (S)—N-[2-(1,6,7,8-tetrahydro-2H-indeno[5,4-b]furan-8-yl)ethyl]propionamide of the above-mentioned [29], wherein the bipolar disorder is bipolar disorder I.

[33] The (S)—N-[2-(1,6,7,8-tetrahydro-2H-indeno[5,4-b]furan-8-yl)ethyl]propionamide of the above-mentioned [29], wherein the prophylaxis and/or treatment of the bipolar disorder is a treatment of a depression symptom associated with the bipolar disorder or maintenance of a remission phase of the bipolar disorder.

[34] The method of the above-mentioned [19]-[23], wherein (S)—N-[2-(1,6,7,8-tetrahydro-2H-indeno[5,4-b]furan-8-yl)ethyl]propionamide is administered as the preparation of the above-mentioned [5]-[7], or [9]-[18].

[35] The drug of the above-mentioned [24]-[28], wherein (S)—N-[2-(1,6,7,8-tetrahydro-2H-indeno[5,4-b]furan-8-yl)ethyl]propionamide is administered as the preparation of the above-mentioned [5]-[7], or [9]-[18].

[36] The (S)—N-[2-(1,6,7,8-tetrahydro-2H-indeno[5,4-b]furan-8-yl)ethyl]propionamide of the above-mentioned [29]-[33], which is administered as the preparation of the above-mentioned [5]-[7], or [9]-[18].

Effect of the Invention

According to the present invention, a rapidly disintegrating preparation superior in the disintegration property, a preparation with improved medicament bioavailability and production methods thereof and the like can be provided.

The rapidly disintegrating preparations [1] to [7] of the present invention contain a medicament in granules, and a disintegrant as an extragranule component. Even when a medicament (e.g., compound A etc.) with poor compatibility with the disintegrant is to be used, therefore, an influence of the disintegrant on the medicament can be reduced, thus improving the stability of the medicament.

The rapidly disintegrating preparation of the present invention can improve disintegration property by enclosing a component that prevents disintegration (e.g., masking agent, binder etc.) in granules. In addition, it can achieve high disintegration property by ensuring the invasion route of water into the preparation by coating the component that prevents disintegration with sugar or sugar alcohol. Moreover, in the rapidly disintegrating preparation of the present invention, a medicament is coated with sugar or sugar alcohol. Therefore, the dissolution property of the medicament from the preparation can be improved even when the medicament has high surface hydrophobicity, by altering the surface to be hydrophilic.

The rapidly disintegrating preparation of the present invention can achieve both the good disintegration property and the good preparation hardness.

Among the rapidly disintegrating preparations [1] to [7] of the present invention, the rapidly disintegrating preparations [5] to [7] for oral-mucosal absorption of the present invention are expected to provide an immediate effect by absorption of the medicament from the oral mucosa.

The rapidly disintegrating preparation for oral-mucosal absorption of the present invention can improve bioavailability by increasing the blood concentration of a medicament (e.g., compound A etc.) susceptible to a first pass effect by oral administration. In addition, the rapidly disintegrating preparation for oral-mucosal absorption of the present invention can suppress inconsistent absorption of such medicaments, and further, inconsistent effectiveness as medicaments. Moreover, the rapidly disintegrating preparation for oral-mucosal absorption of the present invention can afford a low dose medicament and a compact preparation based on the improved medicament bioavailability.

According to the production method of the present invention, the rapidly disintegrating preparations [1] to [7] of the present invention having the above-mentioned effects can be produced.

DESCRIPTION OF EMBODIMENTS

The rapidly disintegrating preparation of the present invention is explained in detail in the following.

The rapidly disintegrating preparation of the present invention contains granules comprising a medicament coated with a coating layer containing sugar or sugar alcohol, and a disintegrant.

While the medicament to be used in the present invention is not particularly limited, for example, antipyretic analgesic antiphlogistic drugs, antipsychotic drugs, antianxiety drugs, antidepressant drugs, sedative-hypnotic drugs, gastrointestinal drugs, antacid drugs, antitussive expectorant drugs, antihypertensive agents, drugs for diabetes, drugs for osteoporosis, skeleton muscle relaxants, anti-cancer agents and the like can be recited.

In the rapidly disintegrating preparation of the present invention, the content of the medicament is generally 0.03-50 wt %, preferably 0.03-20 wt %, more preferably 0.03-3 wt %, relative to the total weight of the preparation.

The rapidly disintegrating preparation of the present invention contains a disintegrant as an extragranule component, and therefore, an influence of the disintegrant on the medicament can be reduced even when a medicament having poor compatibility with the disintegrant is used, and the medicament stability can be improved. Thus, the present invention is particularly effective when a medicament having poor compatibility with the disintegrant (e.g. compound A, etc) is used as a medicament.

Compound A is a known therapeutic agent for sleep disorders, which is disclosed in U.S. Pat. No. 6,034,239 and the like, and can be produced by a known method such as the method described in this document and the like.

In the rapidly disintegrating preparation of the present invention, an excipient is contained in granules comprising a medicament coated with a coating layer containing sugar or sugar alcohol.

Examples of the excipient include starches such as corn starch and the like; sugar or sugar alcohols such as lactose, fructose, glucose, mannitol (e.g., D-mannitol), sorbitol (e.g., D-sorbitol), erythritol (e.g., D-erythritol), sucrose and the like: anhydrous calcium phosphate, microcrystalline cellulose, micromicrocrystalline cellulose, powdered glycyrrhiza, sodium hydrogen carbonate, calcium phosphate, calcium sulfate, calcium carbonate, precipitated calcium carbonate, calcium silicate and the like, and corn starch, D-mannitol and microcrystalline cellulose are preferable.

The content of the excipient is generally 13-94 wt %, preferably 54-94 wt %, more preferably 81-93 wt %, relative to the total weight of the preparation.

The rapidly disintegrating preparation of the present invention may further contain an additive, where necessary, in the granules comprising a medicament.

Examples of the additive optionally contained in the granules comprising a medicament include binder, masking agent, solubilizer and the like, which may be used in combination where necessary.

Examples of the binder include starches such as potato starch, wheat starch, rice starch, partly pregelatinized starch, pregelatinized starch, porous starch and the like, hydroxypropylcellulose, hydroxypropylmethylcellulose, polyvinylpyrrolidone, gelatin, starch, gum arabic powder, tragacanth, carmellose, sodium alginate, pullulan, glycerol and the like, and partly pregelatinized starch, hydroxypropylcellulose and pregelatinized starch are preferable.

The content of the binder is generally 0.5-20 wt %, preferably 0.5-15 wt %, more preferably 1-10 wt %, relative to the total weight of the preparation.

Examples of the masking agent include various flavoring agents (thaumatin, sucralose, saccharin, aspartame, xylitol, citric acid, L-sodium glutamate etc.), various receptor antagonists (BENECOAT, sodium chloride etc.), various cation channel antagonists (L-arginine etc.), various clathration agents (α-cyclodextrin, β-cyclodextrin etc.), various flavors (strawberry flavor, mint flavor, orange flavor, vanillin etc.) and the like. Two or more thereof may be used in combination where necessary.

The content of the masking agent is generally 0.01-10 wt %, preferably 0.01-5 wt %, more preferably 0.01-1 wt %, relative to the total weight of the preparation.

Examples of the solubilizer include various aqueous solvents (polyethylene glycol, propylene glycol, glycerol etc.), various clathration agents (α-cyclodextrin, β-cyclodextrin etc.), various surfactants (sodium lauryl sulfate, polysorbate 80, polyoxyethylene(160)polyoxypropylene(30)glycol etc.) and the like. Two or more thereof may be used in combination where necessary.

The content of the solubilizer is generally not more than 20 wt %, preferably not more than 15 wt %, more preferably not more than 10 wt %, relative to the total weight of the preparation.

In the rapidly disintegrating preparation of the present invention, disintegration property can be improved by including a component that prevents disintegration (e.g., masking agent, binder, solubilizer etc.) in granules. In addition, as mentioned below, the preparation can achieve high disintegration property by ensuring the invasion route of water into the preparation by coating the component that prevents disintegration with sugar or sugar alcohol.

The rapidly disintegrating preparation of the present invention contains sugar or sugar alcohol in a coating layer formed on the granules comprising a medicament.

Examples of the sugar or sugar alcohol include lactose, fructose, glucose, mannitol (e.g., D-mannitol), sorbitol (e.g., D-sorbitol), erythritol (e.g., D-erythritol), sucrose and the like, and D-mannitol is preferable.

The preparation can achieve high disintegration property by ensuring the invasion route of water into the preparation by coating the granules comprising a medicament with sugar or sugar alcohol. In addition, the dissolution property of the medicament from the preparation can be improved.

The content of the sugar contained in the coating layer is generally 5-20 wt %, preferably 5-15 wt %, more preferably 5-10 wt %, relative to the total weight of the preparation.

The content of the sugar alcohol contained in the coating layer is generally 5-20 wt %, preferably 5-15 wt %, more preferably 5-10 wt %, relative to the total weight of the preparation.

The content of the sugar and sugar alcohol contained in the coating layer is generally 5-20 wt %, preferably 5-15 wt %, more preferably 5-10 wt %, relative to the total weight of the preparation.

The rapidly disintegrating preparation of the present invention may further contain an additive in the coating layer as necessary.

Examples of the additive optionally contained in the coating layer include excipient, disintegrant and the like, which may be used in combination as necessary.

Examples of the excipient include starches such as corn starch and the like; anhydrous calcium phosphate, microcrystalline cellulose, micromicrocrystalline cellulose, powdered glycyrrhiza, sodium hydrogen carbonate, calcium phosphate, calcium sulfate, calcium carbonate, precipitated calcium carbonate, calcium silicate and the like, and corn starch and microcrystalline cellulose are preferable.

Examples of the disintegrant include amino acid, starch, corn starch, carmellose, carmellose sodium, carmellose calcium, croscarmellose sodium, crospovidone, low-substituted hydroxypropylcellulose, hydroxypropyl starch, sodium carboxymethyl starch and the like, and crospovidone and carmellose are preferable.

In the rapidly disintegrating preparation of the present invention, the average particle size of the "granules comprising a medicament coated with a coating layer containing sugar or sugar alcohol" is generally 50 μm-500 μm, preferably 50 μm-355 μm, more preferably 50 μm-150 μm.

In the present specification, the average particle size is a value measured by a laser diffraction particle size analyzer, SYMPATEC:HELOS&RODOS and the like.

In the rapidly disintegrating preparation of the present invention, examples of the disintegrant contained as an extragranule component include amino acid, starch, corn starch, carmellose, carmellose sodium, carmellose calcium, croscarmellose sodium, crospovidone, low-substituted hydroxypropylcellulose, hydroxypropyl starch, sodium carboxymethyl starch and the like, and crospovidone and carmellose are preferable.

The content of the disintegrant is generally 0.5-15 wt %, preferably 1-10 wt %, more preferably 2-5 wt %, relative to the total weight of the preparation.

In the rapidly disintegrating preparation of the present invention, examples of the lubricant optionally contained as an extragranule component include magnesium stearate, stearic acid, calcium stearate, talc (purified talc), sucrose esters of fatty acid, sodium stearyl fumarate and the like, and sodium stearyl fumarate is preferable.

The content of the lubricant is generally 0.5-2 wt %, preferably 0.5-1.5 wt %, more preferably 0.5-1 wt %, relative to the total weight of the preparation.

The rapidly disintegrating preparation of the present invention may further contain an additive as an extragranule component where necessary.

Examples of the additive include masking agent, solubilizer and the like, explained above, which may be used in combination where necessary.

The rapidly disintegrating preparation of the present invention is not only useful as a so-called "orally disintegratable preparation" aiming at oral administration of a medicament, but also preferable as a preparation for oral-mucosal absorption (particularly, sublingual preparation, buccal preparation).

The rapidly disintegrating preparation for oral-mucosal absorption of the present invention can be expected to show immediate effect by absorption from the oral mucosa.

The rapidly disintegrating preparation for oral-mucosal absorption of the present invention is particularly effective when a medicament (e.g., compound A etc.) susceptible to a first pass effect by oral administration is used. The rapidly disintegrating preparation for oral-mucosal absorption of the present invention can improve bioavailability by increasing the blood concentration of such medicament. In addition, the rapidly disintegrating preparation for oral-mucosal absorption of the present invention can suppress inconsistent absorption of such medicaments, and further, inconsistent effectiveness as medicaments. Moreover, the rapidly disintegrating preparation for oral-mucosal absorption of the present invention can afford a low dose medicament and a compact preparation based on the improved medicament bioavailability.

When compound A is particularly used as a medicament, the rapidly disintegrating preparation for oral-mucosal absorption of the present invention shows an effect in that the ratio of the medicament in an unchanged form and a metabolite of the medicament after transfer into blood is higher than that by oral administration. In addition, the rapidly disintegrating preparation for oral-mucosal absorption of the present invention shows not less than about 10-fold improved bioavailability of compound A, as compared to that by oral administration.

While the dosage form of the rapidly disintegrating preparation of the present invention is not particularly limited, it is preferably a tablet.

When the rapidly disintegrating preparation of the present invention is a tablet, the weight of the preparation is preferably about 20-200 mg.

When the rapidly disintegrating preparation of the present invention is a tablet, the absolute hardness is generally not less than 1.0 N/mm$^2$, preferably not less than 1.5 N/mm$^2$, more preferably not less than 2.0 N/mm$^2$. When the rapidly disintegrating preparation of the present invention is a tablet, the absolute hardness is generally not more than 5.0 N/mm$^2$.

When the rapidly disintegrating preparation of the present invention is a tablet, the disintegration time is generally not more than 30 sec, preferably not more than 15 sec, more preferably not more than 10 sec. When the rapidly disintegrating preparation of the present invention is a tablet, the disintegration time is generally not less than 1 sec.

In the rapidly disintegrating preparation of the present invention, the disintegration property can be improved by including, in granules, a component that prevents disintegration, as described above. In addition, it can achieve high disintegration property by ensuring the invasion route of water into the preparation by coating the component that prevents disintegration with sugar or sugar alcohol. Therefore, even when the rapidly disintegrating preparation of the present invention is molded to have the above-mentioned high absolute hardness, it shows good disintegration property. Thus, the rapidly disintegrating preparation of the present invention can achieve both the good disintegration property and the good preparation hardness.

The rapidly disintegrating preparation of the present invention preferably shows a disintegration time of not more than 30 sec, and absolute hardness of not less than 1.0 N/mm$^2$.

The rapidly disintegrating preparation of the present invention can be produced by a method conventionally used in the pharmaceutical-technical field. For example, the preparation can be produced by the following production method of the rapidly disintegrating preparation of the present invention.

The production method of the rapidly disintegrating preparation of the present invention includes
step (1): producing granules comprising a medicament,
step (2): forming a coating layer containing sugar or sugar alcohol on the obtained granules, and
step (3): mixing the coated granules with a disintegrant and molding the mixture.

In steps (1)-(3), an additive may be further added as necessary. As the kind and amount of the "medicament", "sugar", "sugar alcohol", "disintegrant" and "additive" to be used in steps (1)-(3), those exemplified for the above-mentioned rapidly disintegrating preparation can be mentioned. As the particle size of the coated granules obtained in step (2), the range exemplified as the particle size of the "granules comprising a medicament coated with a coating layer containing sugar or sugar alcohol" of the above-mentioned rapidly disintegrating preparation can be mentioned.

The production of the granule in step (1) and formation of the coating layer in step (2) can also be carried out simultaneously.

For example, the preparation can be specifically produced as follows.

Sugar or sugar alcohol (e.g., D-mannitol etc.) is dissolved in a suitable solvent (e.g., water etc.) to give a coating solution.

A medicament (e.g., compound A etc.) and any additive (e.g., excipient such as D-mannitol, microcrystalline cellulose and the like, binder such as partly pregelatinized starch and the like etc.) are mixed to give a mixture. The obtained mixture is granulated while spraying the coating solution thereon, and dried to give a granulated powder (coated granules). The obtained granulated powder (coated granules) may be sieved as necessary.

The obtained coated granules, a disintegrant (e.g., crospovidone etc.) and any additive (e.g., lubricant such as sodium stearyl fumarate etc., and the like) are mixed to give a mixed powder. The obtained mixed powder is compression-molded to give a tablet.

Here, the mixing (including granulation, drying, sieving and the like) is carried out by using a preparation machine, for example, V-type mixer, tumbler mixer (TM-30, TM-15S; SHOWA KAGAKU KIKAI CO., LTD.: TM20-0-0; Suchiro Kakoki Co., Ltd.), high speed mixer granulator (FM-VG-10; POWREX CORPORATION), universal kneader (HATA IRON WORKS CO., LTD.), fluid bed dryer granulator (LAB-1, FD-3S, FD-3SN, FD-5S; POWREX CORPORATION), box type vacuum dryer (Kusuki Kikai Seisakusho), power mill grinding machine (P-3, SHOWA KAGAKU KIKAI CO., LTD.), centrifugation rolling granulator (CF-mini, CF-260, CF-360; Freund Corporation), dry type granulator, spray-drying granulator, rolling granulator (MP-10; POWREX CORPORATION) and the like.

Coating is carried out by using, for example, a preparation machine, for example, centrifugation rolling granulator (CF-mini, CF-260, CF-360; Freund Corporation), rolling granulator (MP-10; POWREX CORPORATION), general fluidized bed coater, wurster-type coater and the like.

Compression molding is carried out by using, for example, single punch tableting machine (Kikusui Seisakusho Ltd.), rotary tableting machine (AQUARIUS 36K, AQUARIUS 2L; Kikusui Seisakusho Ltd.), AUTOGRAPH (AG-5000B, SHIMADZU Corporation) and the like, and by punching generally at a pressure of 1-30 kN.

In addition to the application of the above-mentioned "rapidly disintegrating preparation of the present invention" to compound A, the present inventors have intensively studied a preparation superior in the absorption of compound A from the oral mucosa and having improved bioavailability of compound A, and completed the following invention.

That is, the present invention also relates to a preparation for oral-mucosal absorption containing compound A as a medicament; which shows a higher ratio of the medicament in an unchanged form and a metabolite of the medicament after transfer into blood than that by oral administration (preparations [9] to [11], [17] and [18]) (hereinafter sometimes to be abbreviated as preparation (A) of the present invention).

When the dosage form of preparation (A) is a tablet, the disintegration time is preferably not more than 30 sec. When the dosage form in preparation (A) is a tablet, more preferably, the disintegration time is not more than 30 sec, and the absolute hardness is not less than 1.0 N/mm$^2$.

The aforementioned preparations [5] to [7] are also encompassed in the "preparation (A)".

The present invention also relates to a preparation for oral-mucosal absorption, which contains compound A, and shows not less than about 10-fold improved bioavailability of compound A, as compared to that by oral administration (preparations [12] to [18]) (hereinafter sometimes to be abbreviated as preparation (B) of the present invention). Here, "about" means 5% error range. The bioavailability is generally improved within the range of not more than about 30-fold, more specifically not more than about 20-fold.

When the dosage form of preparation (B) is a tablet, preferably, the disintegration time is not more than 30 sec. When the dosage form in preparation (B) is a tablet, more preferably, the disintegration time is not more than 30 sec, and the absolute hardness is not less than 1.0 N/mm$^2$.

The aforementioned preparations [5] to [7] are also encompassed in the "preparation (B)".

Here, whether or not "bioavailability of compound A is improved not less than about 10-fold as compared to oral administration" is evaluated as follows.

Each preparation is administered intravenously, orally or oral-mucosally, the plasma concentration after lapse of each time period is measured, and the area under the plasma concentration time curve (AUC) is calculated according to the trapezoidal rule. In addition, bioavailability (BA) is calculated according to the following formula.

$$BA\ (\%) = (\text{oral or oral-mucosal administration AUC}/\text{intravenous administration AUC}) \times 100.$$

The ratio of the calculated BA by oral-mucosal administration relative to the calculated BA by oral administration (that is, BA by oral-mucosal administration/BA by oral administration) is calculated.

In this case, when the "ratio of the BA by oral-mucosal administration relative to the BA by oral administration" is not less than 10, the preparation is evaluated to show "not less than about 10-fold improved bioavailability of compound A as compared to that by oral administration".

As for the specific preparations to be subjected to a test and test methods, the below-mentioned Experimental Example 3 can be referred to. However, when a substantially similar evaluation is possible, the method is not limited to that of Experimental Example 3.

The present invention also relates to a preparation for oral-mucosal absorption, which contains compound A and shows a higher ratio of a medicament in an unchanged form and a metabolite of the medicament after transfer into blood than that by oral administration (preparations [9] to [11]) (hereinafter sometimes to be abbreviated as preparation (C) of the present invention).

The "greater than the ratio" specifically means not less than about 5-fold, preferably not less than about 10-fold. It is generally not more than about 30-fold, more specifically not more than about 20-fold. Here, "about" means 5% error range.

When the dosage form of preparation (C) is a tablet, preferably, the disintegration time is not more than 30 sec. When the dosage form of preparation (C) is a tablet, more preferably, disintegration time is not more than 30 sec, and the absolute hardness is not less than 1.0 N/mm².

The aforementioned preparations [5] to [7] are also encompassed in the "preparation (C)".

Here, whether or not the "ratio of the medicament in an unchanged form and a metabolite of the medicament after transfer into blood is higher than that by oral administration" is evaluated as follows.

Each preparation is administered orally or oral-mucosally, the plasma concentration of both the unchanged form and metabolite after lapse of each time period is measured, and the area under the plasma concentration time curve (AUC) of the both is calculated according to the trapezoidal rule. The ratio of the unchanged form and metabolite (i.e., AUC of unchanged form/AUC of metabolite) in each preparation is calculated.

In this case, when the ratio by oral-mucosal administration is higher than that by oral administration, it is evaluated "the ratio of a medicament in an unchanged form and a metabolite of the medicament after transfer into blood is higher than that by oral administration".

As for the specific preparations to be subjected to a test and test methods, the below-mentioned Experimental Example 4 can be referred to. However, when a substantially similar evaluation is possible, the method is not limited to that of Experimental Example 4.

While the dosage forms of preparation (A), preparation (B) and preparation (C) are not particularly limited as long as they can be administered from the oral mucosa. For example, tablet (e.g., sublingual tablet, buccal tablet), film, troche, solution, suspension, freeze-dried preparation, chewing gum, spray and the like can be mentioned. Among these, tablet is preferable.

As the kind and amount of "compound A", "masking agent", "sugar", "sugar alcohol" and "disintegrant" to be used for preparation (A), preparation (B) or preparation (C), those exemplified for the above-mentioned rapidly disintegrating preparation can be mentioned.

In the present specification, the absolute hardness is hardness per unit area, and is defined according to the following formula.

$$\text{absolute hardness (N/mm}^2\text{)} = \text{hardness (N)}/(\text{thickness (mm)} \times \text{diameter (mm)})$$

In the present invention, the tablet hardness can be measured by a tablet hardness tester (TH-303MP, Toyama Sangyo CO., LTD.).

In the present specification, the disintegration time is a value measured by a disintegration tester (ODT-101, Toyama Sangyo CO., LTD.) for orally rapidly disintegrating tablet.

Preparations (A)-(C) can be produced, for example, according to the production method explained for "the rapidly disintegrating preparation of the present invention". Particularly, when the dosage form of preparations (A)-(C) is tablet, such production method is preferable. It is also possible to apply other techniques for orally disintegrating preparations.

When the dosage form of preparations (A)-(C) is film, the preparations can be produced according to a conventional method as follows. For example, the preparation can be produced by applying or spraying a coating solution (solution or suspension, solvent is, for example, purified water) containing a medicament, a film carrier, other film carriers used as necessary and the like to the surface of a support medium, and drying same (JP-B-3460538).

When the dosage form of preparations (A)-(C) is freeze-dried preparation, the preparation can be produced according to a conventional method as follows. For example, the preparation can be produced by mixing a medicament, a polymer, sugars and the like, and dissolving and lyophilizing them (Manufacturing Chemist, Feb. 36 (1990)).

When the dosage form of preparations (A)-(C) is chewing gum, the preparation can be produced according to a conventional method as follows. For example, the preparation can be produced by adding a medicament, additive such as sweetener, flavor, colorant, softening agent, flavoring substance and the like to a gum base containing a resin for a gum base as a main component, wax, an emulsifier and a filler, uniformly kneading them in a kneader, and processing them into a plate form, a block form and the like (JP-A-2009-136240).

When the dosage form of preparations (A)-(C) is troche, the preparation can be produced according to a general production method of tablets.

When the dosage form of preparations (A)-(C) is solution or suspension, the preparation can be produced according to a general production method of liquids.

When the dosage form of preparations (A)-(C) is spray, the preparation can be produced according to a general production method of spray.

The preparation of the present invention can be safely administered to a mammal (e.g., human, mouse, rat, rabbit, dog, cat, bovine, horse, swine, monkey), particularly human.

The dose of the preparation of the present invention varies depending on the subject of administration, administration route, disease and the like. For example, when a preparation for oral-mucosal absorption containing compound A as a medicament is administered to an adult, the dose of compound A is about 0.0002—about 0.02 mg/kg body weight, preferably about 0.0002—about 0.01 mg/kg body weight, more preferably about 0.0002—about 0.005 mg/kg body weight, most preferably about 0.0002—about 0.004 mg/kg body weight, which can be administered in one to several portions a day.

It is known that melatonin secretion decreases to cause disorders in the circadian rhythm in patients with bipolar disorders. Compound A is a superior melatonin receptor agonist, and considered to be effective for the prophylaxis or treatment of diseases possibly influenced by melatonin. In fact, compound A is suggested to be effective for the treatment of bipolar disorders (particularly maintenance of remission phase) in the clinical evaluation by oral administration.

As mentioned above, the present invention provides a preparation showing superior absorption of compound A from the oral mucosa and improved bioavailability thereof. Hence, a more effective method for the prophylaxis and/or treatment of bipolar disorders, and a more effective drug for the prophylaxis and/or treatment of bipolar disorders are provided.

To be precise, by oral-mucosal administration of compound A to patients affected with bipolar disorders, the bipolar disorders can be prevented and/or treated. Specifically, such prophylaxis and/or treatment can be performed by appropriately administering the preparation of the present invention to humans.

Here, the administration route of compound A is preferably sublingual administration or buccal administration, and sublingual administration is particularly preferable.

While the dose of compound A is as mentioned above, for administration as a sublingual tablet or a buccal tablet, for example, a tablet containing 0.05-1.5 mg (preferably, 0.05-1.0 mg, more preferably, 0.1-1.0 mg, and most preferably, 0.1 mg, 0.4 mg and 0.8 mg) of compound A per tablet is preferably administered to patients in one to three portions (preferably once) per day.

As the target disease, it is particularly effective for bipolar disorder I. Specifically, it is effective for the "treatment of depression symptoms (particularly, acute depression symptoms) associated with bipolar disorder" and "maintenance of remission phase of bipolar disorder".

For the "prophylaxis and/or treatment of bipolar disorders by oral-mucosal administration of compound A", other medicaments for the prophylaxis and/or treatment of bipolar disorders may be used in combination. Such other medicaments for the prophylaxis and/or treatment of bipolar disorders to be used in combination with "compound A" (hereinafter referred to as "combination medicament") may include mood stabilizer (e.g. lithium, valproic acid, carbamazepine, lamotrigine, etc) and antipsychotics (e.g. quetiapine, olanzapine, etc), and a combination of one or more medicaments selected from them. In addition thereto, one or more SSRI (selective serotonin reuptake inhibitors) (e.g. fluvoxamine, paroxetine, escitalopram, fluoxetine, citalopram, etc) may also be administered in combination with "compound A" and the aforementioned "combination medicament".

The administration mode of the "combination medicament" is not particularly restricted, and it is sufficient that "compound A" and "combination medicament" be combined in administration. Examples of such administration mode include the following:
(1) administration of a single preparation obtained by simultaneously processing "compound A" and "combination medicament",
(2) simultaneous administration of two kinds of preparations of "compound A" and "combination medicament", which have been separately produced, by the same administration route,
(3) administration of two kinds of preparations of "compound A" and "combination medicament", which have been separately produced, by the same administration route in a staggered manner,
(4) simultaneous administration of two kinds of preparations of "compound A" and "combination medicament", which have been separately produced, by different administration routes,
(5) administration of two kinds of preparations of "compound A" and "combination medicament", which have been separately produced, by different administration routes in a staggered manner (e.g., administration in the order of "compound A" and "combination medicament", or in the reverse order) and the like.

The dosage of the "combination medicament" may be determined according to the dose clinically used, and can be appropriately selected depending on an administration subject, administration route, seriousness of the disease, combination, and the like.

The "combination medicament" can be administered in the same dosage form as clinically used or in a different dosage form suitable for this combination therapy.

When compound A is administered oral-mucosally to a human subject, the blood kinetic of it is quite similar to that of the endogenous melatonin, and therefore compound A can regulate circadian rhythm, which is thought to be disturbed in bipolar patients, better than existing drugs and even melatonin/other melatonin agonists. Thus, compound A is expected to show superior effect on bipolar disease to existing drugs. In addition, this circadian rhythm regulating effect can also translate into better normalizing circadian rhythm and/or sleep/awake cycle in bipolar patients.

EXAMPLES

The present invention is explained in more detail in the following by referring to Examples, which are not to be construed as limitative. The preparation additives (e.g., D-mannitol, microcrystalline cellulose, and the like) used in the following Examples and Comparative Examples were the Japanese Pharmacopoeia 15th Edition or Japanese Pharmaceutical Excipients 2003 compatible products.

Example 1

(1) D-Mannitol (PEARLITOL 50C, Roquette) (450.0 g) was dissolved in purified water (2550 g) to give a coating solution. Compound A (150.5 g), D-mannitol (3068 g), microcrystalline cellulose (CEOLUS PH-101, Asahi Kasei Corporation) (112.5 g), and partly pregelatinized starch (PCS, Asahi Kasei Corporation) (450.0 g) were uniformly mixed in a fluid bed dryer granulator (FD-5S, POWREX CORPORATION), granulated while spraying the coating solution (3000 g), and dried to give a granulated powder. A part of the obtained granulated powder was ground in a power mill grinding machine (P-3, SHOWA KAGAKU KIKAI CO., LTD.) using a 1.5 mm$\phi$ punching screen to give a sieved powder.
(2) To the obtained sieved powder (1692 g) were added crospovidone (Kollidon CL-F, BASF) (90 g) and sodium stearyl fumarate (PRUV, JRS PHARMA) (18 g), and the mixture was mixed in a tumbler mixer (TM-30, SHOWA KAGAKU KIKAI CO., LTD.) to give a mixed powder.
(3) The mixed powder was tableted by a rotary tableting machine (AQUA 08242L2JI, Kikusui Seisakusho Ltd.) using a 4 mm$\phi$ punch (tableting pressure: 4 kN, weight per tablet: 30 mg) to give a tablet.

Composition of Preparation (30 mg)

| | |
|---|---|
| compound A | 1.0 mg |
| D-mannitol (in granules) | 20.45 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Comparative Example 1

Polyethylene glycol 400 (PEG400) (Wako Pure Chemical Industries, Ltd.) (15 g) was dissolved in purified water (35 g) to give PEG400 solution. Compound A (12.5 mg) was added to PEG400 solution (50 ml), and the mixture was stirred and insonated, and filtered using a hydrophilic filter (0.45 μm). The obtained compound A solution was divided into small portions (1 ml each).

Composition of Preparation (1 ml)

| | |
|---|---|
| compound A | 0.25 mg |
| PEG400 | 300.0 mg |
| purified water | 700.0 mg |
| total | 1000.25 mg |

Comparative Example 2

(1) Hydroxypropylcellulose (HPC-L, NIPPON SODA CO., LTD.) (40 g) was dissolved in purified water (627 g) to give a binding solution. Compound A (2.5 g), lactose (DMV INTERNATIONAL) (1053.5 g), and corn starch (Japan Corn Starch Co., Ltd.) (160 g) were uniformly mixed in a fluid bed dryer granulator (MP-01, POWREX CORPORATION), granulated while spraying the binding solution (667 g), and dried to give a granulated powder. The obtained granules were sieved through a 16 mesh (aperture 1.0 mm) sieve to give a sieved powder.

(2) Corn starch (17 g) and magnesium stearate (5 g) were added to the obtained sieved powder (628 g) and mixed in a bag to give a mixed powder.

(3) The mixed powder was tableted by a rotary tableting machine (compact tableting machine, Kikusui Seisakusho Ltd.) by using a 4 mmφ punch (tableting pressure: 7 kN, weight per tablet: 130 mg) to give a tablet (core tablet).

(4) Hydroxypropylmethylcellulose (TC-5R) (22.44 g) and Copovidone (4.5 g) were dissolved in purified water (198 g) and dispersed therein to give dispersion I. Titanium oxide (25 g) and yellow ferric oxide (0.5 g) were dispersed in purified water (450 g) to give dispersion II. Dispersion II was added to dispersion I, and the mixture was stirred to give a coating solution. The coating solution was sprayed on the core tablet obtained in (3) until the weight of the core tablet increased by 5 mg per tablet by using a coater (High Coater HC-LAB0, Freund Corporation) to give a film-coated tablet having the following composition.

Composition of Preparation (135 mg)

| | |
|---|---|
| compound A | 0.25 mg |
| lactose | 105.35 mg |
| corn starch | 19.4 mg |
| hydroxypropylcellulose | 4.0 mg |
| magnesium stearate | 1.0 mg |
| hydroxypropylmethylcellulose | 3.74 mg |
| Copovidone | 0.75 mg |
| titanium oxide | 0.5 mg |
| yellow ferric oxide | 0.01 mg |
| total | 135 mg |

Example 2

(1) D-Mannitol (PEARITOL 50C, Roquette) (120 g) was dissolved in purified water (680 g) to give a coating solution. Compound A (10 g), D-mannitol (848 g), microcrystalline cellulose (CEOLUS PH-101, Asahi Kasei Corporation) (30 g), and partly pregelatinized starch (PCS, Asahi Kasei Corporation) (120 g) were uniformly mixed in a fluid bed dryer granulator (MP-01, POWREX CORPORATION), granulated while spraying a coating solution (800 g), and dried to give a granulated powder. The obtained granules were sieved through a 16 mesh (aperture 1.0 mm) sieve to give a sieved powder.

(2) The obtained sieved powder (28.2 g), crospovidone (Kollidon CL-F, BASF) (1.5 g) and sodium stearyl fumarate (0.3 g) were mixed in a glass bottle. The obtained mixture was tableted (tableting pressure: 3 KN/punch, tablet weight per tablet: 30 mg) by an AUTOGRAPH (AG-5000B, SHIMADZU Corporation) using a 4 mmφ punch to give a core tablet with the following composition.

Composition of Preparation (30 mg)

| | |
|---|---|
| compound A | 0.25 mg |
| D-mannitol (in granules) | 21.2 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Comparative Example 3

PEG400 (Wako Pure Chemical Industries, Ltd.) (60 g) was dissolved in purified water (110 g) to give PEG400 solution. Compound A (100.0 mg) was added to the PEG400 solution (100 ml), and the mixture was stirred and insonated, and filtered using a hydrophilic filter (0.45 μm). The obtained compound A solution was divided into small portions (1 ml each).

Composition of Preparation (1 ml)

| | |
|---|---|
| compound A | 1.0 mg |
| PEG400 | 352.9 mg |
| purified water | 647.1 mg |
| total | 1001 mg |

Comparative Example 4

(1) Hydroxypropylcellulose (HPC-L, NIPPON SODA CO., LTD.) (660 g) was dissolved in purified water (10230 g) to give a binding solution. Compound A (165.3 g), lactose (DMV INTERNATIONAL) (17260 g), and corn starch (Japan Corn Starch Co., Ltd.) (2640 g) were uniformly mixed in a fluid bed dryer granulator (FD-S2, POWREX CORPORATION), granulated while spraying a binding solution (10890 g), and dried to give a granulated powder. This granulation step was performed twice. A part of the obtained granulated powder was ground by a power mill grinding machine (P-3, SHOWA KAGAKU KIKAI CO., LTD.) using a 1.5 mmϕ punching screen to give a sieved powder.

(2) Corn starch (1013 g) and magnesium stearate (298 g) were added to the obtained sieved powder (37430 g), and the mixture was mixed in a tumbler mixer (TM20-0-0, Suchiro Kakoki Co., Ltd.) to give a mixed powder.

(3) The mixed powder was tableted by a rotary tableting machine (AQUARIUS 36K, Kikusui Seisakusho Ltd.) by using a 7 mmϕ punch (tableting pressure: 7 kN, weight per tablet: 130 mg) to give a tablet (core tablet).

(4) Hydroxypropylmethylcellulose (TC-5R, Shin-Etsu Chemical Co., Ltd.) (1548 g) and Copovidone (310.5 g) were dissolved in purified water (16150 g) and dispersed therein to give dispersion I. Titanium oxide (207 g) and yellow ferric oxide (4.14 g) were dispersed in purified water (1822 g) to give dispersion II. Dispersion II was added to dispersion I, and the mixture was stirred to give a coating solution. Using a coater (High Coater HCF-100N, Freund Corporation), the coating solution was sprayed on the core tablet obtained in (3) until the weight of the core tablet increased by 5 mg per tablet to give a film-coated tablet having the following composition.

Composition of Preparation (135 mg)

| compound A | 1.0 mg |
|---|---|
| lactose | 104.6 mg |
| corn starch | 19.4 mg |
| hydroxypropylcellulose | 4.0 mg |
| magnesium stearate | 1.0 mg |
| hydroxypropylmethylcellulose | 3.74 mg |
| Copovidone | 0.75 mg |
| titanium oxide | 0.5 mg |
| yellow ferric oxide | 0.01 mg |
| total | 135 mg |

Example 3

(1) D-mannitol (PEARLITOL 50C, Roquette) (120 g) was dissolved in purified water (680 g) to give a coating solution. Compound A (40 g), D-mannitol (818 g), microcrystalline cellulose (CEOLUS PH-101, Asahi Kasei Corporation) (30 g), and partly pregelatinized starch (PCS, Asahi Kasei Corporation) (120 g) were uniformly mixed in a fluid bed dryer granulator (MP-01, POWREX CORPORATION), granulated while spraying the coating solution (800 g), and dried to give a granulated powder. The obtained granules were sieved through a 16 mesh (aperture 1.0 mm) sieve to give a sieved powder.

(2) The obtained sieved powder (28.2 g), crospovidone (Kollidon CL-F, BASF) (1.5 g) and sodium stearyl fumarate (0.3 g) were mixed in a glass bottle. The obtained mixture was tableted (tableting pressure: 3 KN/punch, tablet weight per tablet: 30 mg) by an AUTOGRAPH (AG-5000B, SHIMADZU Corporation) by using a 4 mmϕ punch to give a core tablet with the following composition.

Composition of Preparation (30 mg)

| compound A | 1.0 mg |
|---|---|
| D-mannitol (in granules) | 20.45 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Example 4

Compound A (5 g) and CMEC (20 g) were dissolved in acetone:ethanol=3:2 mixed solution (500 ml), and spray-dried by a spray dryer (Pulvis Mini Spray, YAMATO SCIENTIFIC CO., LTD.). The obtained solid dispersion powder was dried in vacuo at 40° C. for 16 hr. To the solid dispersion powder (0.5 g) was added D-mannitol (PEARLITOL 100SD, Roquette) (11.5 g) and mixed in a bottle. The obtained mixed powder was divided into small portions (120 mg each).

Composition of Preparation (120 mg)

| compound A | 1.0 mg |
|---|---|
| CMEC | 4.0 mg |
| D-mannitol | 115.0 mg |
| total | 120 mg |

Example 5

Hydroxypropyl-β-cyclodextrin (hereinafter sometimes referred to as HP-β-CyD) (KLEPTOSE HPB, Roquette) (75 g) was dissolved in purified water (422.5 g). Compound A (2.5 g) was dissolved in the obtained HP-β-CyD aqueous solution to give a coating solution. D-Mannitol (PEARLITOL 50C, Roquette) (200 g) and microcrystalline cellulose (CEOLUS PH-101, Asahi Kasei Corporation) (7.5 g) were uniformly mixed in a fluid bed dryer granulator (MP-01, POWREX CORPORATION), granulated while spraying the coating solution (500 g), and dried to give a granulated powder. The obtained granules were sieved through a 16 mesh (aperture 1.0 mm) sieve to give a sieved powder. The obtained sieved powder was divided into small portions (114 mg each).

Composition of Preparation (114 mg)

| compound A | 1.0 mg |
|---|---|
| HP-β-CyD | 30.0 mg |
| D-mannitol | 80.0 mg |
| microcrystalline cellulose | 3.0 mg |
| total | 114 mg |

Example 6

(1) D-Mannitol (PEARLITOL 50C, Roquette) (450 g) was dissolved in purified water (2550 g) to give a coating solution. Compound A (37.6 g), D-mannitol (3180 g), microcrystalline cellulose (CEOLUS PH-101, Asahi Kasei Corporation) (112.5 g), and partly pregelatinized starch (PCS, Asahi Kasei Corporation) (450 g) were uniformly mixed in a fluid bed dryer granulator (FD-5S, POWREX CORPORATION), granulated while spraying the coating solution (3000 g), and dried to give a granulated powder. A part of the obtained granulated powder was ground by a power mill grinding machine (P-3, SHOWA KAGAKU KIKAI CO., LTD.) using a 1.5 mmφ punching screen to give a sieved powder.

(2) Crospovidone (Kollidon CL-F, BASF) (90 g) and sodium stearyl fumarate (18 g) were added to the obtained sieved powder (1692 g), and the mixture was mixed in a tumbler mixer (TM-15S, SHOWA KAGAKU KIKAI CO., LTD.) to give a mixed powder.

(3) The mixed powder was tableted by a rotary tableting machine (AQUARIUS 2L, Kikusui Seisakusho Ltd.) by using a 4 mmφ punch (tableting pressure: 4 kN, weight per tablet: 30 mg) to give a core tablet with the following composition.

Composition of Preparation (30 mg)

| | |
|---|---|
| compound A | 0.25 mg |
| D-mannitol (in granules) | 21.2 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Example 7

(1) D-mannitol (PEARLITOL 50C, Roquette) (450 g) was dissolved in purified water (2550 g) to give a coating solution. Compound A (150.5 g), D-mannitol (3068 g), microcrystalline cellulose (CEOLUS PH-101, Asahi Kasei Corporation) (112.5 g), and partly pregelatinized starch (PCS, Asahi Kasei Corporation) (450 g) were uniformly mixed in a fluid bed dryer granulator (FD-5S, POWREX CORPORATION), granulated while spraying the coating solution (3000 g), and dried to give a granulated powder. A part of the obtained granulated powder was ground by a power mill grinding machine (P-3, SHOWA KAGAKU KIKAI CO., LTD.) using a 1.5 mmφ punching screen to give a sieved powder.

(2) Crospovidone (Kollidon CL-F, BASF) (90 g) and sodium stearyl fumarate (18 g) were added to the obtained sieved powder (1692 g), and the mixture was mixed in a tumbler mixer (TM-15S, SHOWA KAGAKU KIKAI CO., LTD.) to give a mixed powder.

(3) The mixed powder was tableted by a rotary tableting machine (AQUARIUS 2L, Kikusui Seisakusho Ltd.) by using a 4 mmφ punch (tableting pressure: 4 kN, weight per tablet: 30 mg) to give a core tablet with the following composition.

Composition of Preparation (30 mg)

| | |
|---|---|
| compound A | 1.0 mg |
| D-mannitol (in granules) | 20.45 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| total | 30 mg |

Comparative Example 5

(1) Hydroxypropylcellulose (HPC-L, NIPPON SODA CO., LTD.) (660 g) was dissolved in purified water (10230 g) to give a binding solution. Compound A (1320 g), lactose (DMV INTERNATIONAL) (16104 g), and corn starch (Japan Corn Starch Co., Ltd.) (2640 g) were uniformly mixed in a fluid bed dryer granulator (FD-S2, POWREX CORPORATION), granulated while spraying the binding solution (10890 g), and dried to give a granulated powder. This granulation step was performed twice. A part of the obtained granulated powder was ground by a power mill grinding machine (P-3, SHOWA KAGAKU KIKAI CO., LTD.) using a 1.5 mmφ punching screen to give a sieved powder.

(2) Corn starch (1013 g) and magnesium stearate (298 g) were added to the obtained sieved powder (37430 g), and the mixture was mixed in a tumbler mixer (TM20-0-0, Suchiro Kakoki Co., Ltd.) to give a mixed powder.

(3) The mixed powder was tableted by a rotary tableting machine (AQUARIUS 36K, Kikusui Seisakusho Ltd.) by using a 7 mmφ punch (tableting pressure: 7 kN, weight per tablet: 130 mg) to give a tablet (core tablet).

(4) Hydroxypropylmethylcellulose (TC-5R, Shin-Etsu Chemical Co., Ltd.) (1548 g) and Copovidone (310.5 g) were dissolved and dispersed in purified water (16150 g) to give dispersion I. Titanium oxide (207 g) and yellow ferric oxide (4.14 g) were dispersed in purified water (1822 g) to give dispersion II. Dispersion II was added to dispersion I, and the mixture was stirred to give a coating solution. Using a coater (High Coater HCF-100N, Freund Corporation), the coating solution was sprayed on the core tablet obtained in (3) until the weight of the core tablet increased by 5 mg per tablet to give a film-coated tablet having the following composition.

Composition of Preparation (135 mg)

| | |
|---|---|
| compound A | 8.0 mg |
| lactose | 97.6 mg |
| corn starch | 19.4 mg |
| hydroxypropylcellulose | 4.0 mg |
| magnesium stearate | 1.0 mg |
| hydroxypropylmethylcellulose | 3.74 mg |
| Copovidone | 0.75 mg |
| titanium oxide | 0.5 mg |
| yellow ferric oxide | 0.01 mg |
| total | 135 mg |

Example 8

(1) D-Mannitol (PEARLITOL 50C, Roquette) (510 g) was dissolved in purified water (2890 g) to give a coating solution. Compound A (17.05 g), D-mannitol (3114 g), microcrystalline cellulose (CEOLUS PH-101, Asahi Kasei Corporation) (127.5 g), and partly pregelatinized starch (PCS, Asahi Kasei Corporation) (510 g) were uniformly mixed in a fluid bed dryer granulator (FD-5S, POWREX CORPORATION), granulated while spraying the coating solution (3400 g), and dried to give a granulated powder. A part of the obtained granulated powder was sieved using a round sieve (mesh size 1.0 mmφ) to give sieved powder A.

(2) The same step as (1) was performed to give sieved powder B.

(3) To the obtained sieved powder A (3146.5 g) and sieved powder B (3146.5 g) were added crospovidone (Kollidon CL-F, BASF) (375.0 g), aspartame (750 g), vanillin (7.5 g) and sodium stearyl fumarate (75 g), and the mixture was mixed in a tumbler mixer (TM-60S, SHOWA KAGAKU KIKAI CO., LTD.) to give a mixed powder.

(4) The mixed powder was tableted by a rotary tableting machine (AQUARIUS 2L, Kikusui Seisakusho Ltd.) using a 4 mmφ punch (tableting pressure: 4 kN, weight per tablet: 30 mg) to give a core tablet with the following composition.

Composition of Preparation (30 mg)

| | |
|---|---|
| compound A | 0.1 mg |
| D-mannitol (in granules) | 18.32 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| aspartame | 3.0 mg |
| vanillin | 0.03 mg |
| total | 30 mg |

Example 9

(1) D-Mannitol (PEARLITOL 50C, Roquette) (510 g) was dissolved in purified water (2890 g) to give a coating solution. Compound A (68.20 g), D-mannitol (3063 g), microcrystalline cellulose (CEOLUS PH-101, Asahi Kasei Corporation) (127.5 g), and partly pregelatinized starch (PCS, Asahi Kasei Corporation) (510 g) were uniformly mixed in a fluid bed dryer granulator (FD-5S, POWREX CORPORATION), granulated while spraying the coating solution (3400 g), and dried to give a granulated powder. A part of the obtained granulated powder was sieved by using a round sieve (mesh size 1.0 mmφ) to give sieved powder A.

(2) The same step as (1) was performed to give sieved powder B.

(3) To the obtained sieved powder A (3146.5 g) and sieved powder B (3146.5 g) were added crospovidone (Kollidon CL-F, BASF) (375.0 g), aspartame (750 g), vanillin (7.5 g) and sodium stearyl fumarate (75 g), and the mixture was mixed in a tumbler mixer (TM-60S, SHOWA KAGAKU KIKAI CO., LTD.) to give a mixed powder.

(4) The mixed powder was tableted by a rotary tableting machine (AQUARIUS 2L, Kikusui Seisakusho Ltd.) using a 4 mmφ punch (tableting pressure: 4 kN, weight per tablet: 30 mg) to give a core tablet with the following composition.

Composition of Preparation (30 mg)

| | |
|---|---|
| compound A | 0.4 mg |
| D-mannitol (in granules) | 18.02 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| aspartame | 3.0 mg |
| vanillin | 0.03 mg |
| total | 30 mg |

Example 10

(1) D-Mannitol (PEARLITOL 50C, Roquette) (510 g) was dissolved in purified water (2890 g) to give a coating solution. Compound A (136.4 g), D-mannitol (2995 g), microcrystalline cellulose (CEOLUS PH-101, Asahi Kasei Corporation) (127.5 g), and partly pregelatinized starch (PCS, Asahi Kasei Corporation) (510 g) were uniformly mixed in a fluid bed dryer granulator (FD-5S, POWREX CORPORATION), granulated while spraying the coating solution (3400 g), and dried to give a granulated powder. A part of the obtained granulated powder was sieved by using a round sieve (mesh size 1.0 mmφ) to give sieved powder A.

(2) The same step as (1) was performed to give sieved powder B.

(3) To the obtained sieved powder A (3146.5 g) and sieved powder B (3146.5 g) were added crospovidone (Kollidon CL-F, BASF) (375.0 g), aspartame (750 g), vanillin (7.5 g) and sodium stearyl fumarate (75 g), and the mixture was mixed in a tumbler mixer (TM-60S, SHOWA KAGAKU KIKAI CO., LTD.) to give a mixed powder.

(4) The mixed powder was tableted by a rotary tableting machine (AQUARIUS 2L, Kikusui Seisakusho Ltd.) using a 4 mmφ punch (tableting pressure: 4 kN, weight per tablet: 30 mg) to give a core tablet with the following composition.

Composition of Preparation (30 mg)

| | |
|---|---|
| compound A | 0.8 mg |
| D-mannitol (in granules) | 17.62 mg |
| D-mannitol (in coating layer) | 3.0 mg |
| microcrystalline cellulose | 0.75 mg |
| partly pregelatinized starch | 3.0 mg |
| crospovidone | 1.5 mg |
| sodium stearyl fumarate | 0.3 mg |
| aspartame | 3.0 mg |
| vanillin | 0.03 mg |
| total | 30 mg |

Experimental Example 1

The tablet obtained in Example 1 was measured for the tablet hardness and disintegration time. The tablet hardness was measured by a tablet hardness tester (TH-303MP, Toyama Sangyo CO., LTD.) (n=10). The disintegration time was measured by a disintegration tester (ODT-101, Toyama Sangyo CO., LTD.) (n=6). The results are shown in Table 1.

Disintegration Tester Conditions
rotation number: 50 rpm
plummet: 15 mmφ, (10 g)

TABLE 1

| | |
|---|---|
| hardness | 21N |
| absolute hardness | 2.73 N/mm$^2$ |
| disintegration | 5.24 sec |

Experimental Example 2

The mixed powder obtained in Example 1 was measured for the dissolution property. The mixed powder (15 g) (corresponding to 500 mg of compound A) was placed in the Japanese Pharmacopoeia 2nd fluid (500 ml), and the dissolution property was evaluated by the Paddle Method, rotation number 25 rpm, 37° C. After adding the sample, the eluate was sampled with time (0.25 min, 0.5 min, 0.75 min, 1 min, 5 min, 15 min, 30 min), filtered by using a hydrophilic filter (0.45 μm), dissolved by 10-fold diluting with the extract (water/acetonitrile mixed solution (1:1)), and quantified by high performance liquid column chromatography (HPLC) under the following conditions to calculate the solubility. The results are shown in Table 2.

HPLC Conditions
detector: ultraviolet ray absorption spectrophotometer measurement wavelength: 240 nm
column: YMC-Pack ODS-AM AM-307, 5 μm, inner diameter: 4.6 mm length: 75 mm
column temperature: 25° C.
mobile phase: 0.01 mol/L phosphate buffer/acetonitrile mixed solution (5:3)
flow: 1.2 ml/min

TABLE 2

| time (min) | compound A concentration (mg/ml) |
|---|---|
| 0 | 0 |
| 0.25 | 0.103 |
| 0.5 | 0.218 |
| 0.75 | 0.225 |
| 1 | 0.237 |
| 5 | 0.273 |
| 15 | 0.279 |
| 30 | 0.280 |

Experimental Example 3

The injections obtained in Comparative Examples 1, 3, oral tablets obtained in Comparative Examples 2, 4 and preparations for oral-mucosal absorption obtained in Examples 2-5 were measured for blood kinetics after intravenous injection, oral, sublingual and buccal administrations in *Macaca fascicularis* under fasting conditions. The plasma concentration before administration, and 5 min, 10 min, 20 min, 30 min, 60 min, 120 min, 240 min and 360 min after administration was measured, and the area under the plasma concentration time curve (AUC) was calculated according to the trapezoidal rule. In addition, bioavailability (BA) was determined by calculating the ratio of AUC by oral, sublingual or buccal administration to AUC by intravenous injection. The results are shown in Table 3.

TABLE 3

| dose (mg) | administration route | preparation | $T_{max}$ (min) | $C_{max}$ (ng/ml) | AUC (ng · min/ml) | BA (%) |
|---|---|---|---|---|---|---|
| 0.25 | intravenous injection | Comparative Example 1 | 9.0 ± 6.5 | 63.4 ± 14.1 | 2933.8 ± 578.5 | — |
| | oral | Comparative Example 2 | 132.0 ± 130.1 | 0.4 ± 0.1 | 54.4 ± 22.6 | 1.9 |
| | sublingual | Example 2 | 34.0 ± 15.2 | 12.5 ± 5.9 | 1218.0 ± 655.8 | 41.5 |
| | buccal | Example 6 | 36.0 ± 18.0 | 22.7 ± 12.3 | 1656.0 ± 726.0 | 56.4 |
| 1 | intravenous injection | Comparative Example 3 | 3.2 ± 1.6 | 509.7 ± 248.9 | 16889.5 ± 2057.2 | — |
| | oral | Comparative Example 4 | 8.0 ± 13.0 | 0.8 ± 1.2 | 21.3 ± 35.8 | 0.1 |
| | sublingual | Example 3 | 28.0 ± 4.5 | 38.5 ± 12.8 | 3062.4 ± 1129.9 | 18.1 |
| | | Example 4 | 42.0 ± 16.0 | 31.4 ± 8.6 | 3206.9 ± 809.9 | 19.0 |
| | | Example 5 | 48.0 ± 16.0 | 46.6 ± 13.8 | 4568.4 ± 1286.3 | 27.0 |
| | buccal | Example 7 | 36.0 ± 12.0 | 87.1 ± 21.2 | 5862.0 ± 1038.0 | 34.7 |

Experimental Example 4

Oral preparation and preparation for oral-mucosal absorption were measured for blood kinetics of unchanged form and activity metabolite M-II after oral or sublingual administration to human. The plasma concentration before administration, and 5 min, 10 min, 15 min, 20 min, 30 min, 45 min, 60 min, 90 min, 120 min, 180 min, 240 min, 360 min, 480 min, 600 min, 720 min and 1440 min after administration was measured, and the area under the plasma concentration time curve (AUC) was calculated according to the trapezoidal rule. The results are shown in Table 4.

TABLE 4

| measurement substance | dose (mg) | administration route | preparation | $T_{max}$ (min) | $C_{max}$ (ng/ml) | AUC(0-tlqc) (ng · min/ml) | AUC(0-inf) (ng · min/ml) |
|---|---|---|---|---|---|---|---|
| unchanged form | 8 | oral | Comparative Example 8 | 45.0 (19.8-120.0) | 4.76 ± 5.19 | 364.8 ± 383.0 | 334.2 ± 347.6 |
|  | 0.5 | sublingual | Example 6 | 15.0 (9.0-30.0) | 4.74 ± 1.52 | 215.4 ± 64.6 | 223.8 ± 67.1 |
| active metabolite M-II | 8 | oral | Comparative Example 8 | 60.0 (30.0-180.0) | 68.1 ± 23.2 | 12495.0 ± 4998.0 | 12747.0 ± 5098.8 |
|  | 0.5 | sublingual | Example 6 | 45.0 (15.0-60.0) | 4.18 ± 1.26 | 596.4 ± 280.3 | 730.8 ± 285.0 |

Example 10

A methylcellulose powder (0.5 g) was dissolved in water (99.5 g) under ice-cooling, and compound A (100 mg) was added to the obtained solution (10 ml), stirred and uniformly dispersed therein. The obtained suspension was filled in a spray device (spray amount: 100 μL/time) to give an oral spray preparation.

Example 11

Hydroxypropyl-β-cyclodextrin (HP-β-CyD) (40 g) was dissolved in water (60 g), and compound A (100 mg) was added to the obtained solution (10 ml), stirred and dissolved therein. The obtained solution was filled in a spray device (spray amount: 100 μL/time) to give an oral spray preparation.

Example 12

Compound A (100 mg), polyvinylpyrrolidone (1 g) and hydroxypropylcellulose (18 g) were added to ethanol (100 ml) and dissolved by stirring. The obtained solution (1 ml) was spread flat on a plastic sheet and dried to give an orally rapidly dissolving film preparation.

Example 13

Compound A (100 mg), D-mannitol (5 g) and hydroxypropylcellulose (100 mg) were added to a mixed solution (100 ml) of water and ethanol (4:1) and dissolved by stirring. The obtained solution (1 ml) was dispensed to a pocket of a blister pack with vinyl chloride resin as an inner film, frozen at −30° C., and dried by a vacuum dryer to give an orally rapidly dissolving freeze-dried preparation.

INDUSTRIAL APPLICABILITY

The present invention can provide a novel preparation showing improved bioavailability of a medicament and a production method thereof and the like.

When compound A is administered nasally (through nasal mucosa) to a human subject, it is expected to be effective on prophylaxis and/or treatment of bipolar disease as administered oral-mucosally as disclosed above. Compound A can be administered, for example, in the form of the formulation as disclosed in WO 01/15735.

When compound A is administered to a human subject, it can be also administered in the dosage forms suitable for inhalation (e.g. nebulizer, etc) in order to prevent and/or treat bipolar disease. The dosage forms can be produced according to a general production method in this art. The dose of compound A can be decided referring to, for example, the preparations (A) to (C) in the present application.

The invention claimed is:

1. A method for the treatment of a bipolar disorder comprising administering an effective amount of (S)—N-[2-(1,6,7,8-tetrahydro-2H-indeno[5,4-b]furan-8-yl)ethyl]propionamide (compound A) oral-mucosally to a human in need thereof, wherein (S)—N-[2-(1,6,7,8-tetrahydro-2H-indeno[5,4-b]furan-8-yl)ethyl]propionamide (compound A) is administered at a dose of 0.05-1.0 mg per day.

2. A method for the treatment of a bipolar disorder comprising administering an effective amount of (S)—N-[2-(1,6,7,8-tetrahydro-2H-indeno[5,4-b]furan-8-yl)ethyl]propionamide (compound A) oral-mucosally to a human in need thereof, wherein (S)—N-[2-(1,6,7,8-tetrahydro-2H-indeno[5,4-b]furan-8-yl)ethyl]propionamide (compound A) is administered at a dose of 0.1-0.8 mg per day.

3. The method according to claim 1, wherein the oral-mucosal administration is sublingual administration or buccal administration.

4. The method according to claim 2, wherein the oral-mucosal administration is sublingual administration or buccal administration.

5. The method according to claim 1, wherein (S)—N-[2-(1,6,7,8-tetrahydro-2H-indeno[5,4-b]furan-8-yl)ethyl]propionamide (compound A) is administered in the form of a rapidly disintegrating preparation for oral-mucosal absorption comprising granules comprising compound A coated with a coating layer comprising sugar or sugar alcohol; and a disintegrant.

6. The method according to claim 1, wherein the treatment of a bipolar disorder is selected from the group consisting of treatment of a depression symptom associated with the bipolar disorder or maintenance of a remission phase of the bipolar disorder.

7. The method according to claim 6, wherein the depression symptom associated with the bipolar disorder is acute depression.

8. The method according to claim 2, wherein the treatment of a bipolar disorder is selected from the group consisting of treatment of a depression symptom associated with the bipolar disorder or maintenance of a remission phase of the bipolar disorder.

9. The method according to claim 8, wherein the depression symptom associated with the bipolar disorder is acute depression.

10. The method according to claim 1, wherein the dosage of 0.05-1.0 mg is administered in one portion a day.

* * * * *